(12) United States Patent
Hedenberg

(10) Patent No.: US 6,539,975 B2
(45) Date of Patent: Apr. 1, 2003

(54) ARRANGEMENT FOR MAINTAINING GAS IN A VARIABLE VOLUME CONTAINER AT A CONSTANT PRESSURE

(75) Inventor: Håkan Hedenberg, Järfälla (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 10/062,936

(22) Filed: Jan. 31, 2002

(65) Prior Publication Data
US 2002/0104539 A1 Aug. 8, 2002

(30) Foreign Application Priority Data
Feb. 7, 2001 (SE) .............................................. 0100378

(51) Int. Cl.[7] .............................................. F16L 55/04
(52) U.S. Cl. .............................. 138/31; 138/30; 138/26
(58) Field of Search ................. 138/26, 30, 31

(56) References Cited

U.S. PATENT DOCUMENTS

| 1,145,601 | A | * | 7/1915 | Lemoine | 137/116.3 |
|---|---|---|---|---|---|
| 1,522,931 | A | * | 1/1925 | Wirz | 138/31 |
| 1,601,668 | A | * | 9/1926 | Beals | 137/424 |
| 2,353,692 | A | * | 7/1944 | Cunningham | 91/368 |
| 2,415,812 | A | * | 2/1947 | Cunningham | 138/31 |
| 3,824,902 | A |   | 7/1974 | Olsson | 92/40 |
| 3,979,910 | A | * | 9/1976 | Leuenberger et al. | 60/476 |

FOREIGN PATENT DOCUMENTS

| DE | 37 12 388 | 10/1988 |
|---|---|---|
| DE | 37 12 389 | 10/1988 |

* cited by examiner

*Primary Examiner*—Patrick Brinson
(74) *Attorney, Agent, or Firm*—Schiff Hardin & Waite

(57) ABSTRACT

A gas container has a gas inlet, a gas outlet, a variable-volume chamber connected to the gas inlet and the gas outlet and a constant force applicator acting on the variable-volume chamber so that constant gas pressure prevails in the variable-volume chamber, regardless of variations in the chamber's volume. The constant force applicator is formed by a spring and a force transfer mechanism that interact with each other through a center of rotation (14) and an application point. The force transfer mechanism varies the distance between the center of rotation and the application point according to the variation in the volume of the variable-volume chamber.

5 Claims, 1 Drawing Sheet

ARRANGEMENT FOR MAINTAINING GAS IN A VARIABLE VOLUME CONTAINER AT A CONSTANT PRESSURE

BACKGROUND OF THE INVENTION

1. Field of the Invention

The present invention relates to a gas container of the type suitable for use for intermediately storing fresh gas in an anesthetic machine.

2. Description of the Prior Art

The use of gas containers for intermediate storage of fresh gas in anesthetic machines before the gas is sent to a breathing circuit is known. For simple regulation of the flow of fresh gas to the breathing circuit, the gas in the gas container is kept at constant pressure, around 100 cmH$_2$O. Since the gas container usually contains a variable-volume reservoir, keeping the pressure constant is no simple matter.

One way to achieve a constant pressure, regardless of the prevailing volume, is to place a weight on the reservoir and allow gravity to exert a constant pressure on the gas in the container. This greatly increases the weight of the apparatus.

Another way is to use a relatively simple spring, with the reservoir's variable-volume space being designed so that it compensates for variations in the spring's compressive force on the reservoir whenever a wall of this space moves.

Other known ways entail the use of special resilient materials for the reservoir or spring designs producing a constant force within certain reservoir volume ranges.

Although these known methods for achieving a constant pressure do work satisfactorily, there is a need for additional alternative solutions. In particular, solutions combining good efficiency with simple design would be advantageous.

SUMMARY OF THE INVENTION

An object of the present invention is to provide a gas container for maintaining a constant gas pressure as an alternative to the known designs.

The above object is achieved in accordance with the principles of the present invention in a gas container having a gas inlet, a gas outlet, a variable-volume chamber connected to the gas inlet and the gas outlet, and a constant force applicator acting on the variable-volume chamber so that a constant gas pressure prevails therein, regardless of variations in the volume of the chamber, and wherein the constant force applicator is formed by a spring and a force transfer mechanism that interact with each other through a center of rotation and an application point, and wherein the force transfer mechanism varies the distance between the center of rotation and the application point dependent on variations in the volume of the variable-volume chamber.

In principle, constant force is obtained by the use of a spring and the force transfer mechanism that interact via a center of rotation and an application point, the center of rotation and the application point being arranged at a variable distance from each other. The ability to move e.g. the center of rotation makes direct compensation possible for variations in the spring force, by shifting the center of rotation. This also applies to the application point.

DESCRIPTION OF THE PREFERRED EMBODIMENTS

Figure 1:
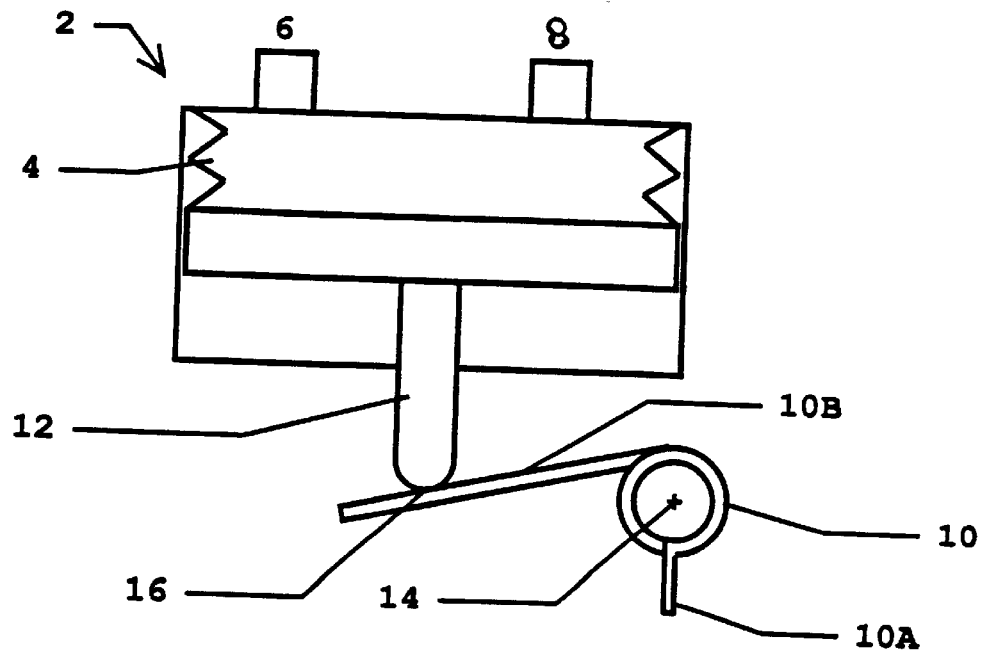
FIG. 1 is a schematic illustration of a first embodiment of the gas container according to the invention.

FIG. 1 shows a first embodiment of a gas container 2 according to the invention. The gas container 2 has a variable-volume chamber 4, i.e. a bellows in this instance, an inlet 6 for gas, and an outlet 8 for gas.

A spring 10 and a rod 12 are arranged to maintain a constant gas pressure in the chamber 4. In this embodiment, the spring 10 is a cylindrical torsion spring with one anchored end 10A (the anchoring not being shown in FIG. 1) and an elongated second end 10B. The second end 10B is able to move in relation to a center of rotation 14. Spring force increases when this end 10B moves downwardly, and spring force decreases when this end 10B moves upwardly. The rod 12 serves as a force transfer mechanism between the spring 10 and the chamber 4. The application point 16 for force from the spring 10 to the rod 12 depends on the vertical position of the rod 12, i.e. the chamber volume. When the chamber volume is maximum, downward movement of the second end 10B is maximum. When the chamber volume is minimum, the second end 10B is essentially horizontal. Since the distance between the center of rotation 14 and the centerline of the rod 12 is constant, the application point 16 (and the vertical force component) will shift according to the angle of the second end 10B to the horizontal plane. The force exerted against the chamber 4 therefore remains constant over the entire range of movement of the rod 12.

Figure 2:
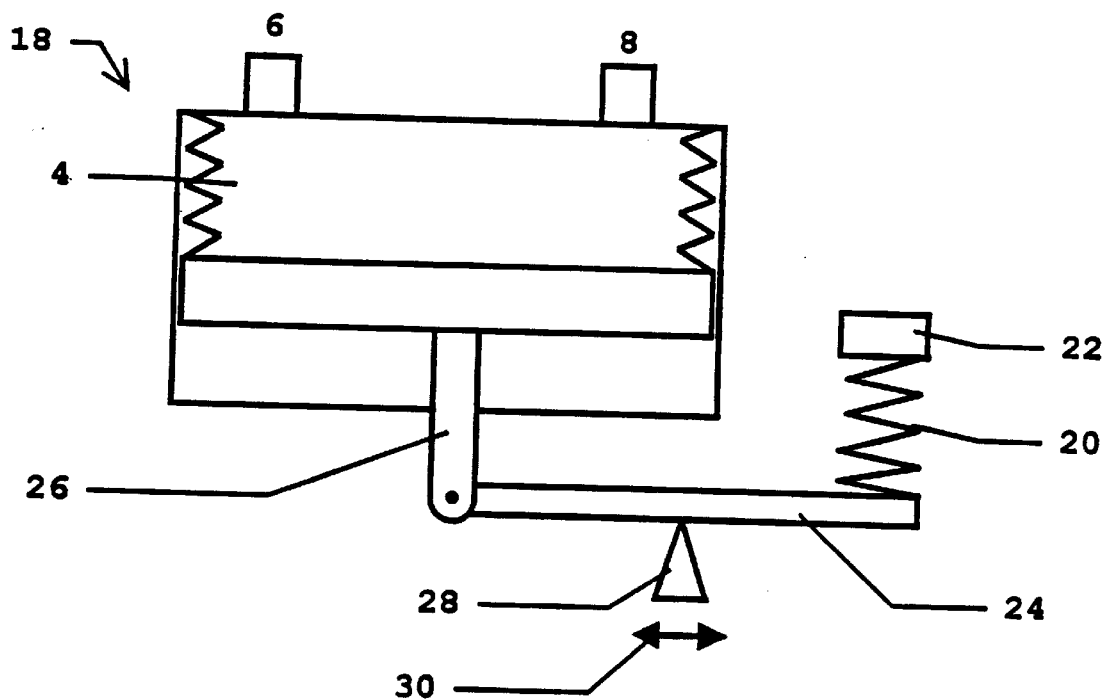
FIG. 2 is a schematic illustration of a second embodiment of the gas container according to the invention.

FIG. 2 shows a second embodiment of a gas container 18. Components that can be identical to components in the embodiment according to FIG. 1 have been assigned the same designations. Thus, the gas container 18 has a variable-volume chamber 4, an inlet 6 and an outlet 8.

The second embodiment differs from the first embodiment in its components for achieving constant pressure in the chamber 4.

A spring 20 (e.g. a pressure spring) is anchored at one end to an abutment 22 and to a beam 24 at its other end. This constitutes the application point for the force. The beam 24, in turn, is connected (by swiveling attachment) to a rod 26 acting on the chamber 4. The beam 24 and the rod 26 jointly constitute a force transfer mechanism.

The beam 24 interacts with a support 28 so that a lever effect is achieved in the transfer of force from the spring 20 to the rod 26. The support 28 then serves as a center of rotation. The support 28 can be moved along the beam 24, as designated by the arrow 30.

Compensation for the spring's variable force is achieved when the support 28 (i.e. the center of rotation) is moved according to the volume of the chamber (e.g. the position of the rod 26). Force exerted against the chamber 4 is therefore constant over the entire range of movement of the rod 26.

Alternatively, the support 28 can be moved according to the pressure measured inside the chamber (not shown in FIG. 2).

Another alternative is to move the support 28 in a vertical rather than a horizontal direction.

Another alternative is to let the support serve as a fixed point of rotation and instead move the spring 20 along the beam 24.

The two embodiments in FIGS. 1 and 2 can be combined. For example, the spring 10 in FIG. 1 can be made moveable in the same way as for the spring 28 in FIG. 2 (horizontal movement). A double effect is then achieved since both the center of rotation and the application point are moved. (The corresponding effect is achieved, according to the example in FIG. 2, when both the support 28 and the spring 20 are moved according to the volume/position/pressure of the chamber 4).

Although modifications and changes may be suggested by those skilled in the art, it is the intention of the inventor to embody within the patent warranted hereon all changes and modifications as reasonably and properly come within the scope of his contribution to the art.

I claim as my invention:

1. A gas container comprising:

a variable-volume chamber;

a gas inlet communicating with said variable volume chamber;

a gas outlet communicating with said variable-volume chamber; and a constant force applicator acting on said variable-volume chamber to maintain a constant gas pressure in said variable-volume chamber regardless of variations in the volume of said variable-volume chamber, said constant force applicator comprising a spring and a force transfer mechanism interacting with each other through a center of rotation and an application point, and wherein said force transfer mechanism alters a distance said center of rotation and said application point dependent on said variation in the volume of said variable volume chamber.

2. A gas container as claimed in claim 1 wherein said center of rotation is substantially stationary, and wherein said force transfer mechanism varies a distance of said application point from said center of rotation dependent on said variation in the volume of the variable volume chamber.

3. A gas container as claimed in claim 2 wherein said spring is a torsion spring having an anchored first end and a substantially horizontal, elongated second end, and wherein said force transfer mechanism comprises a vertically moving rod resting on said second end of said torsion spring.

4. A gas container as claimed in claim 3 wherein said torsion spring is a coiled cylindrical spring.

5. A gas container as claimed in claim 1 wherein said force transfer mechanism is a lever mounted for rotating around said center of rotation, and wherein a position of said center of rotation varies relative to said application point dependent on said variation in the volume of the variable-volume chamber.

* * * * *